United States Patent
Kim et al.

(10) Patent No.: US 11,492,648 B2
(45) Date of Patent: Nov. 8, 2022

(54) MODIFIED POLYPEPTIDE HAVING AN ACTIVITY OF ORNITHINE-BASED PRODUCT EXPORTER AND METHOD FOR PRODUCING ORNITHINE-BASED PRODUCT USING CELLS EXPRESSING THE POLYPEPTIDE

(71) Applicant: CJ CHEILJEDANG CORPORATION, Seoul (KR)

(72) Inventors: Seon Hye Kim, Seoul (KR); Su Jin Park, Seoul (KR); Kyoung Min Lee, Seoul (KR); Kyungsu Na, Seoul (KR); Hong Xian Li, Seoul (KR); Hyun-jung Bae, Seoul (KR); Jihyun Shim, Seoul (KR); Young Lyeol Yang, Seoul (KR); Hye Won Um, Seoul (KR); Hyo Hyoung Lee, Seoul (KR); Min Gyeong Kang, Seoul (KR); Hye Won Kim, Seoul (KR); Byeong Cheol Song, Seoul (KR); Haena Oh, Seoul (KR); Han Hyoung Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/622,490

(22) PCT Filed: Jun. 14, 2018

(86) PCT No.: PCT/KR2018/006732
§ 371 (c)(1),
(2) Date: Dec. 13, 2019

(87) PCT Pub. No.: WO2018/230977
PCT Pub. Date: Dec. 20, 2018

(65) Prior Publication Data
US 2020/0208182 A1 Jul. 2, 2020

(30) Foreign Application Priority Data
Jun. 14, 2017 (KR) .................. 10-2017-0074980

(51) Int. Cl.
| | |
|---|---|
| *C12P 13/10* | (2006.01) |
| *C07K 14/34* | (2006.01) |
| *C12P 13/00* | (2006.01) |
| *C12N 1/20* | (2006.01) |
| *C12R 1/15* | (2006.01) |

(52) U.S. Cl.
CPC .............. *C12P 13/10* (2013.01); *C07K 14/34* (2013.01); *C12P 13/001* (2013.01); *C12Y 306/03* (2013.01); *C12N 1/205* (2021.05); *C12R 2001/15* (2021.05); *C12Y 401/01017* (2013.01)

(58) Field of Classification Search
CPC ..................................................... C12Y 306/03
USPC ........................................................ 435/114
See application file for complete search history.

(56) References Cited

U.S. PATENT DOCUMENTS

| | | | |
|---|---|---|---|
| 6,551,795 B1 * | 4/2003 | Rubenfield | ............ C07K 14/21 435/253.3 |
| 10,221,433 B2 * | 3/2019 | Lee | ............ C12N 9/1096 |
| 2003/0113899 A1 | 6/2003 | Yamaguchi et al. | |

FOREIGN PATENT DOCUMENTS

| | | |
|---|---|---|
| EP | 2 977 443 A1 | 1/2016 |
| JP | 2009-254323 A | 11/2009 |
| KR | 10-0791659 B1 | 1/2008 |
| KR | 10-2012-0064045 A | 6/2012 |
| KR | 10-2013-0082478 A | 7/2013 |
| KR | 10-1372635 B1 | 3/2014 |
| KR | 10-2014-0115244 A | 9/2014 |
| KR | 10-1493585 B1 | 2/2015 |
| KR | 10-1607741 B1 | 3/2016 |
| KR | 10-2017-0000906 A | 1/2017 |
| KR | 10-2017-0010960 A | 2/2017 |

OTHER PUBLICATIONS

Issued Patents database (.RAI) Result 35 SID 30864 from Rubenfield et al, U.S. Pat. No. 6,551,795. Alignment with SID1.*
Bellmann et al., "Expression control and specificity of the basic amino acid exporter LysE of *Corynebacterium glutamicum*," *Microbiology* 147:1765-1744, 2001.
Gotoh et al., "Direct production of L-ornithine from casein by commercial digestive enzymes and in situ activated arginase," *Bioprocess Biosyst Eng* 33:773-777, 2010 (6 pages).
Kim et al., "Metabolic Engineering of *Corynebacterium glutamicum* for the Production of L-Ornithine," *Biotechnology and Bioengineering* 112(2):416-421, 2015.
Matsui et al., "Detection of D-Ornithine Extracellularly Produced by *Corynebacterium glutamicum* ATCC 13032::argF," *Biosci. Biotechnol. Biochem.* 74(12):2507-2510, 2010 (5 pages).
Qian et al., "Metabolic Engineering of *Escherichia coli* for the Production of Putrescine: A Four Carbon Diamine," *Biotechnology and Bioengineering* 104(4):651-662, 2009.
Schneider et al., "Putrescine production by engineered *Corynebacterium glutamicum*," *Appl Microbiol Biotechnol* 88:859-868, 2010.
U.S. Appl. No. 16/622,087, filed Dec. 12, 2019, Novel Polypeptide and Method for Producing Ornithine-Based Product Using the Same.
UNIPROT, Database Accession No. A0A1Q3DSX5, 2 pages, (Apr. 12, 2017).

* cited by examiner

*Primary Examiner* — Sheridan Swope
(74) *Attorney, Agent, or Firm* — Seed IP Law Group LLP

(57) ABSTRACT

The present disclosure relates to a novel polypeptide having an ability to export an ornithine-based product, and a method for producing an ornithine-based product using the same.

19 Claims, No Drawings
Specification includes a Sequence Listing.

MODIFIED POLYPEPTIDE HAVING AN ACTIVITY OF ORNITHINE-BASED PRODUCT EXPORTER AND METHOD FOR PRODUCING ORNITHINE-BASED PRODUCT USING CELLS EXPRESSING THE POLYPEPTIDE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_460USPC_SEQUENCE_LISTING.txt. The text file is 26.3 KB, was created on Dec. 11, 2019, and is being submitted electronically via EFS-Web.

TECHNICAL FIELD

The present disclosure relates to a novel polypeptide having an ability to export an ornithine-based product, and a method for producing an ornithine-based product using the same.

BACKGROUND ART

Ornithine, which is a material widely found in plants, animals, and microorganisms, is biosynthesized from glutamate, and is used as a precursor in the biosynthesis of putrescine, citrulline, and proline. Further, ornithine plays an important role in the pathway for excretion of urea produced from amino acids or ammonia by the ornithine cycle in the in vivo metabolism of higher animals. Ornithine is effective in enhancing muscle growth and reducing body fat and thus is used as nutrient supplements and also as pharmaceutical drugs for improving liver cirrhosis and liver function disorders. The known methods for producing ornithine include treatment of milk casein with digestive enzymes and use of transformed *E. coli* or a microorganism of the genus *Corynebacterium* (Korean Patent No. 10-1372635; T. Gotoh et al., *Bioprocess Biosyst. Eng.*, 33: 773-777, 2010).

Putrescine (or 1,4-butanediamine) is a very important raw material for the production of polyamide-4, 6 including nylon-4, 6, and can be produced on an industrial scale by hydrogenation of succinonitrile, which is produced from acrylonitrile by addition of hydrogen cyanide. The synthesis pathway of these chemical substances requires non-renewable petrochemical products as raw materials. Additionally, high temperature and pressure, which are implicated with the use of expensive catalyst systems, as well as relatively complex preparation steps and equipment are also needed. Accordingly, as an alternative to the chemical production process, a process of producing putrescine from a renewable biomass-derived carbon source is required. Recently, studies have been continuously conducted to use environment-friendly microorganisms for the production of industrially available high-concentration polyamines (putrescine) (Qian Z G, et al., *Biotechnol Bioeng*, 104: 651-662, 2009; Schneider J, et al., *Appl Microbiol Biotechnol*, 88: 859-868, 2010).

Meanwhile, NCgl2522 has been identified as a gene having an ability to export putrescine (Korean Patent No. 2014-0115244). However, in order to produce putrescine in a higher yield, there is still a need to develop a protein with an improved ability to export putrescine which can more effectively export putrescine from a putrescine-producing strain.

L-arginine has been widely used in medicines as hepatic function-promoting agents, brain function-promoting agents, and as ingredients of multiple amino acid supplements. Additionally, L-arginine has gained much interest in food industry as a food additive for fish cakes and health beverages, and as a salt substitute for hypertension patients. Studies have been continuously conducted to use microorganisms for the production of industrially available high-concentration arginine, and examples thereof include a method of using a mutant strain induced from the microorganism belonging to the genus *Brevibacterium* or *Corynebacterium*, which is a glutamate-producing strain, or a method of using an amino acid-producing strain, whose growth is improved through cell fusion. Meanwhile, lysE of the microorganism belonging to the genus *Corynebacterium* having an ability to export L-lysine has also been shown to export the same basic amino acid L-arginine (Bellmann A, et al, *Microbiology*, 147:1765-1774, 2001). Further, a method for enhancing the production ability of L-arginine-producing strains through the enhancement of the gene above has been known (U.S. Patent No. 2002-196232).

DISCLOSURE

Technical Problem

The present inventors have made extensive efforts to develop a variant of an export protein capable of further improving the production ability by enhancing the ability to export an ornithine product, and as a result, it was confirmed that the ability to export an ornithine-based product was enhanced when a modification was introduced on a specific site of the amino acid sequence of the NCgl2522 protein. Accordingly, they have found that putrescine or arginine, which is an ornithine-based product, can be produced in a high yield by introducing the protein variant into putrescine- or arginine-producing strains, thereby completing the present invention.

Technical Solution

One object of the present disclosure is to provide a novel polypeptide having an ability to export an ornithine-based product.

Another object of the present disclosure is to provide a polynucleotide encoding the polypeptide, and a vector comprising the polynucleotide.

Still another object of the present disclosure is to provide a microorganism producing an ornithine-based product, comprising the polypeptide or having an enhanced activity thereof.

Still another object of the present disclosure is to provide a method for producing an ornithine-based product, comprising:

(i) culturing the microorganism of the genus *Corynebacterium* producing an ornithine-based product in a medium; and (ii) recovering an ornithine-based product from the microorganism or the medium obtained above.

Advantageous Effects

The polypeptide having an ability to export an ornithine-based product of the present disclosure shows an excellent activity for exporting an ornithine-based product, and thus, the ability to produce an ornithine-based product can be further improved when such an activity is introduced into a microorganism producing an ornithine-based product.

DETAILED DESCRIPTION OF PREFERRED EMBODIMENTS

The present disclosure will be described in detail as follows. Meanwhile, the explanations and embodiments disclosed in the present disclosure may be applied to other explanations and embodiments, respectively. That is, all combinations of various elements disclosed herein belong to the scope of the present disclosure. Additionally, the scope of the present disclosure should not be limited by the specific descriptions described hereinbelow.

In order to achieve the objects above, an aspect of the present disclosure provides a novel polypeptide having an ability to export an ornithine-based product, wherein the glycine residue at position 77 from the N-terminus of the amino acid sequence of an ornithine-based product-exporting protein is substituted with other amino acids.

As used herein, the ornithine-based product-exporting protein refers to a protein which plays a role in the extracellular export of the products biosynthesized from ornithine as a precursor, and specifically refers to a protein which plays a role in the extracellular export of putrescine or arginine. More specifically, it may be NCgl2522 protein disclosed in Korean Patent Application Publication No. 2014-0115244. The NCgl2522 protein may, for example, consist of an amino acid sequence of SEQ ID NO: 1 or SEQ ID NO: 2, but any sequence having the activity identical to the protein may be included without limitation, and the sequence information thereof can be obtained from GenBank of NCBI, a known database.

The novel polypeptide having an ability to export an ornithine-based product of the present disclosure has a feature in which the glycine residue at position 77 from the N-terminus of the amino acid sequence of an ornithine-based product-exporting protein is substituted with other amino acids, and thus has an improved ability to export an ornithine-based product as compared to a non-modified polypeptide, specifically, a polypeptide having a glycine residue at position 77. The polypeptide having an ability to export an ornithine-based product may be, for example, those in which the glycine at position 77 in the amino acid sequence of an ornithine-based product-exporting protein is substituted with alanine or arginine. Specifically, the polypeptide may be a polypeptide consisting of an amino acid sequence of any one of SEQ ID NO: 3 to SEQ ID NO: 6, or an amino acid sequence having a homology or identity thereto of 70% or more, 80% or more, specifically 85% or more, more specifically 90% or more, even more specifically 95% or more, and even more specifically 99% or more, but is not limited thereto as long as it has an ability to export an ornithine-based product by substitution of glycine at position 77 with other amino acid. Additionally, it should be interpreted that, as an amino acid sequence having such a homology or identity, an amino acid sequence with deletion, modification, substitution, or addition of a part of the sequence also falls within the scope of the present disclosure as long as the amino acid sequence has a biological activity substantially identical or corresponding to the polypeptide consisting of the amino acid sequence of any one of SEQ ID NO: 3 to SEQ ID NO: 6.

As used herein, the term "ornithine-based product" refers to a material which can be biosynthesized from ornithine as a precursor. Specifically, examples of the materials that can be produced by the ornithine cycle include putrescine, citrulline, proline, and arginine, but the material is not limited thereto, as long as it can be biosynthesized from ornithine as a precursor. For example, the ornithine-based product may be putrescine and arginine. Additionally, any material, which can be synthesized from ornithine as a precursor and exported by the novel polypeptide having an ability to export an ornithine-based product of the present disclosure, may be included without limitation.

Another aspect of the present disclosure provides a polynucleotide encoding the polypeptide having an ability to export an ornithine-based product.

The polynucleotide may include a polynucleotide encoding a polypeptide having an amino acid sequence of any one of SEQ ID NO: 3 to SEQ ID NO: 6, or a polypeptide having a homology or identity thereto of 70% or more, 80% or more, specifically 85% or more, more specifically 90% or more, even more specifically 95% or more, and even more specifically 99% or more, but is not limited thereto, as long as it has an activity similar to the polypeptide having an ability to export an ornithine-based product. Additionally, it is apparent that due to codon degeneracy, polynucleotides which can be translated into the protein consisting of the amino acid sequence of SEQ ID NO: 1 or proteins having a homology or identity thereto can also be included. Alternatively, a probe which can be prepared from a known gene sequence, for example, any sequence which hybridizes with a sequence complementary to all or part of the nucleotide sequence under stringent conditions to encode a protein having the activity of the protein consisting of the amino acid sequence of SEQ ID NO: 1, may be included without limitation.

The "stringent conditions" refer to conditions under which specific hybridization between polynucleotides is allowed. Such conditions are specifically disclosed in the literature (e.g., J. Sambrook et al.). For example, the stringent conditions may include conditions under which genes having a high homology or identity, a homology or identity of 80% or more, 85% or more, specifically 90% or more, more specifically 95% or more, even more specifically 97% or more, and even more specifically 99% or more, hybridize with each other, while genes having a homology or identity lower than the above homology or identity do not hybridize with each other; or may include ordinary washing conditions of Southern hybridization, i.e., washing once, specifically two or three times, at a salt concentration and a temperature corresponding to 60° C., 1×SSC, and 0.1% SDS; specifically 60° C., 0.1×SSC, and 0.1% SDS; and more specifically 68° C., 0.1×SSC, and 0.1% SDS.

Hybridization requires that two nucleic acids have complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the present disclosure may also include an isolated nucleic acid fragment complementary to the entire sequence as well as a nucleic acid sequence substantially similar thereto.

Specifically, the polynucleotide having homology may be detected using hybridization conditions including a hybridization step at a $T_m$ value of 55° C. under the above-described conditions. Additionally, the $T_m$ value may be 60° C., 63° C., or 65° C., but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art (Sambrook et al., supra, 9.50-9.51, 11.7-11.8).

As used herein, the term "homology" refers to the degree of correspondence between two given amino acid sequences or nucleotide sequences, and may be expressed as a percentage. In the present disclosure, a homologous sequence having an activity which is identical or similar to that of the given amino acid sequence or nucleotide sequence may be indicated in terms of "% homology".

As used herein, the term "identity" refers to the degree of relevance between two given amino acid sequences or nucleotide sequences. In some cases, the identity is determined by the correspondence between strings of such sequences. For example, the identity may be confirmed using standard software for calculating parameters such as score, identity, and similarity, specifically, BLAST 2.0, or by comparing sequences via southern hybridization experiments under defined stringent conditions, and the defined appropriate hybridization conditions are within the skill of the art, and may be determined by a method well known to those skilled in the art (For example, J. Sambrook et al., *Molecular Cloning, A Laboratory Manual*, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York).

The terms "homology" and "identity" are often used interchangeably with each other.

The sequence homology or identity of conserved polynucleotides or polypeptides may be determined by standard alignment algorithms and can be used together with default gap penalty established by the program being used. Substantially, homologous or identical polynucleotides or polypeptides are generally expected to hybridize to all or at least about 50%, about 60%, about 70%, about 80% or about 90% of the entire length of the target polynucleotides or polypeptides under moderate or high stringent conditions. Polynucleotides that contain degenerate codons instead of codons are also considered in the hybridizing polynucleotides.

Whether any two polynucleotide or polypeptide sequences have a homology or identity of at least 50%, 55%, 60%, 65% 70%, 75%, 80%, 85%, 90%, 95%, 96%, 97%, 98% or 99% with each other, it may be determined by a known computer algorithm such as the "FASTA" program (e.g., Pearson et al, (1988) *Proc. Natl. Acad. Sci. USA* 85: 2444) using default parameters. Alternatively, it may be determined by the Needleman-Wunsch algorithm (Needleman and Wunsch, 1970, *J. Mol. Biol.* 48: 443-453), which is performed using the Needleman program of the EMBOSS package (EMBOSS: The European Molecular Biology Open Software Suite, Rice et al., 2000, *Trends Genet.* 16: 276-277) (preferably, version 5.0.0 or versions thereafter) (GCG program package (Devereux, J., et al., *Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [ED.,] Academic Press, San Diego, 1994, and [CARILLO ETA/.] (1988) *SIAM J Applied Math* 48: 1073). For example, the homology or identity may be determined using BLAST or ClustalW of the National Center for Biotechnology Information (NCBI).

The homology or identity of polynucleotides or polypeptides may be determined by comparing sequence information using, for example, the GAP computer program, such as Needleman et al., (1970), *J Mol Biol.* 48: 443 as disclosed in Smith and Waterman, *Adv. Appl. Math* (1981) 2:482. In summary, the GAP program defines the homology or identity as the value obtained by dividing the number of similarly aligned symbols (i.e. nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al., (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to the comparison between polypeptides or polynucleotides.

Still another aspect of the present invention provides a vector comprising the polynucleotide.

As used herein, the term "vector" refers to a DNA construct containing the nucleotide sequence of a polynucleotide encoding the target polypeptide, which is operably linked to a suitable regulatory sequence such that the target polypeptide can be expressed in an appropriate host. The regulatory sequence may include a promoter capable of initiating transcription, any operator sequence for the control of the transcription, a sequence encoding an appropriate mRNA ribosome-binding domain, and a sequence regulating the termination of transcription and translation. After being transformed into a suitable host cell, the vector may be replicated or function irrespective of the host genome, and may be integrated into the host genome itself.

The vector used in the present disclosure is not particularly limited as long as it can be replicated in a host cell, and any vector known in the art may be used. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc. may be used. The vector that can be used in the present disclosure is not particularly limited, and a known expression vector may be used. Specifically, the vectors pDZ, pACYC177, pACYC184, pCL, pECCG117, pUC19, pBR322, pMW118, pCC1BAC, etc. may be used.

In an embodiment, a polynucleotide encoding a target polypeptide in the chromosome may be replaced with a modified polynucleotide through a vector for intracellular chromosome insertion. The insertion of the polynucleotide into the chromosome may be performed by any method known in the art, for example, homologous recombination, but is not limited thereto.

As used herein, the term "transformation" refers to a process of introducing a vector comprising a polynucleotide encoding a target polypeptide into a host cell, thereby enabling expression of the polypeptide encoded by the polynucleotide in the host cell. As long as the transformed polynucleotide can be expressed in the host cell, it does not matter whether it is inserted into the chromosome of a host cell and located therein or located outside the chromosome, and both cases may be included. For example, the transformation may be carried out via electroporation, calcium phosphate ($CaPO_4$) precipitation, calcium chloride ($CaCl_2$) precipitation, microinjection, a polyethylene glycol (PEG) technique, a DEAE-dextran technique, a cationic liposome technique, a lithium acetate-DMSO technique, etc., but the method is not limited thereto. Additionally, the polynucleotide includes DNA and RNA which encode a target polypeptide. The polynucleotide may be introduced in any form as long as it can be introduced into a host cell and expressed therein. For example, the polynucleotide may be introduced into a host cell in the form of an expression cassette, which is a gene construction including all elements necessary for self-expression. The expression cassette may conventionally include a promoter operably linked to the polynucleotide, a terminator, a ribosome-binding domain, and a stop codon. The expression cassette may be in the form of an expression vector capable of self-replication. Additionally, the polynucleotide may be introduced into a host cell as it is and operably linked to a sequence necessary for its expression in the host cell, but is not limited thereto.

Further, as used above, the term "operably linked" refers to a functional linkage between the above gene sequence and a promoter sequence which initiates and mediates the transcription of the polynucleotide encoding the target polypeptide of the present disclosure.

Still another aspect of the present disclosure provides a microorganism producing an ornithine-based product, comprising the polypeptide having an ability to export an ornithine-based product or having an enhanced activity thereof.

Specifically, the present disclosure provides a microorganism of the genus *Corynebacterium* producing putrescine or arginine, including the polypeptide having an ability to export an ornithine-based product or having an enhanced activity thereof.

As used herein, the term "microorganism" includes all of wild-type microorganisms, or naturally or artificially genetically modified microorganisms, and it may be a microorganism in which a particular mechanism is weakened or enhanced due to insertion of a foreign gene, or enhancement or weakening of the activity of an endogenous gene.

As used herein, the term "microorganism of the genus *Corynebacterium*" may be specifically *Corynebacterium glutamicum, Corynebacterium ammoniagenes, Brevibacterium lactofermentum, Brevibacterium flavum, Corynebacterium thermoaminogenes, Corynebacterium efficiens*, etc., but is not limited thereto. More specifically, the microorganisms of the genus *Corynebacterium* in the present disclosure may be *Corynebacterium glutamicum*, the cell growth and survival of which are hardly affected even when exposed to a high concentration of putrescine or arginine.

As used herein, the term "microorganism of the genus *Corynebacterium* producing an ornithine-based product" refers to a microorganism of the genus *Corynebacterium* having an ability to produce an ornithine-based product naturally or via modification. The microorganism of the genus *Corynebacterium* producing an ornithine-based product may be, but is not particularly limited to, those modified such that the activity of at least one selected from the group consisting of, for example, acetylglutamate synthase, which converts glutamate to N-acetylglutamate, or ornithine acetyltransferase (argJ), which converts N-acetylornithine to ornithine, acetylglutamate kinase (ArgB), which converts N-acetylglutamate to N-acetylglutamyl phosphate, acetyl-gamma-glutamyl-phosphate reductase (ArgC), which converts N-acetylglutamyl phosphate to N-acetylglutamate semialdehyde, and acetylornithine aminotransferase (ArgD), which converts N-acetylglutamate semialdehyde to N-acetylornithine is increased compared to the endogenous activity thereof, in order to enhance the biosynthetic pathway from glutamate to ornithine, thereby improving ornithine productivity.

As used herein, the term "microorganism of the genus *Corynebacterium* producing putrescine or arginine" refers to a microorganism of the genus *Corynebacterium* having an ability to produce putrescine or arginine naturally or via modification. The microorganism of the genus *Corynebacterium* does not produce putrescine, can produce arginine, but the productivity of arginine is remarkably low. Therefore, as used herein, the microorganism of the genus *Corynebacterium* producing putrescine or arginine refers to a native strain itself or a microorganism of the genus *Corynebacterium* in which a foreign gene involved in the putrescine or arginine production mechanism is inserted, or the activity of an endogenous gene is enhanced or weakened, so as to have an improved productivity of putrescine or arginine.

Additionally, the microorganism producing putrescine may be those further modified such that the activity of at least one selected from the group consisting of ornithine carbamoyltransferase (ArgF), which is involved in the synthesis of arginine from ornithine, a protein involved in glutamate export, and acetyltransferase, which acetylates putrescine, is weakened compared to the endogenous activity thereof, and/or may be those modified such that an ornithine decarboxylase (ODC) activity is introduced.

Further, the microorganism producing arginine may be those further modified such that the activity of at least one selected from the group consisting of ornithine carbamoyltransfrase, (ArgF), which is involved in the synthesis of arginine from ornithine, argininosuccinate synthase (argG), argininosuccinate lyase (argH), aspartate ammonia lyase, and aspartate aminotransferase is enhanced, compared to the endogenous activity thereof.

As used herein, the term "enhancement" of activity of a protein means that the activity of a protein is introduced, or the activity is enhanced as compared with the endogenous activity thereof. The "introduction" of the activity means that the activity of a specific polypeptide that the microorganism did not originally have is naturally or artificially expressed.

As used herein, the term "increase" in the activity of a protein as compared with the endogenous activity thereof means that the activity of a protein is improved as compared with the endogenous activity of a protein possessed by a microorganism, or the activity before transformation. The "endogenous activity" refers to the activity of a specific protein originally possessed by the parental strain or a non-modified microorganism prior to transformation thereof, when the traits of the microorganism are altered through genetic modification due to natural or artificial factors, and it can be interchangeably used with the activity before transformation.

Specifically, the enhancement of activity in the present disclosure may be performed by the following methods:

1) a method for increasing the copy number of the polynucleotide encoding the protein;

2) a method for modifying an expression regulatory sequence such that the expression of the polynucleotide is increased;

3) a method for modifying the polynucleotide sequence on a chromosome such that the activity of the protein is enhanced;

4) a method for introducing a foreign polynucleotide exhibiting the activity of the protein or a modified polynucleotide in which the codons of the above polynucleotide have been optimized; and 5) a method for modification to enhance the activity by a combination of the above methods, but the method is not limited thereto.

The increasing of the copy number of the polynucleotide in method 1) above may be performed in the form in which the polynucleotide is operably linked to a vector, or by inserting into a chromosome of a host cell, but is not particularly limited thereto. Specifically, it may be performed by operably linking the polynucleotide encoding the protein of the present disclosure to a vector which can replicate and function regardless of the host cell, and introducing the same into the host cell. Alternatively, it may be performed by a method for increasing the copy number of the polynucleotide in the chromosome of the host cell by operably linking the polynucleotide to a vector which can insert the polynucleotide into the chromosome of the host cell, and introducing the same into the host cell.

Next, the modification of an expression regulatory sequence such that the expression of the polynucleotide is increased in method 2) may be performed by inducing a modification in the sequence through deletion, insertion, or non-conservative or conservative substitution of a nucleic acid sequence, or a combination thereof so as to further enhance the activity of the expression regulatory sequence, or by replacing with a nucleic acid sequence having a stronger activity, but is not particularly limited thereto. Additionally, the expression regulatory sequence may include a promoter, an operator sequence, a sequence encoding a ribosome-binding domain, a sequence regulating the termination of transcription and translation, etc., but is not particularly limited thereto.

A strong heterologous promoter may be linked to the upstream region of the expression unit of the polynucleotide instead of the original promoter. Examples of the strong promoter include CJ7 promoter (Korean Patent No. 0620092 and International Publication No. WO2006/065095), lysCP1 promoter (International Publication No. WO2009/096689), EF-Tu promoter, groEL promoter, aceA or aceB promoter, etc., but the strong promoter is not limited thereto. Further, the modification of the polynucleotide sequence on a chromosome in method 3) may be performed by inducing a modification in the expression regulatory sequence through deletion, insertion, or non-conservative or conservative substitution of a nucleic acid sequence, or a combination thereof so as to further enhance the activity of the polynucleotide sequence, or by replacing the polynucleotide sequence with a polynucleotide sequence modified to have a stronger activity, but is not particularly limited thereto.

Additionally, the introduction a foreign polynucleotide sequence in method 4) may be performed by introducing into a host cell a foreign polynucleotide encoding a protein that exhibits an activity identical or similar to that of the protein above, or a modified polynucleotide in which the codons of the foreign polynucleotide have been optimized. The foreign polynucleotide may be used without limitation by its origin or sequence as long as it exhibits an activity identical or similar to that of the protein. Further, the foreign polynucleotide may be introduced into a host cell after optimization of its codons so as to achieve the optimized transcription and translation in the host cell. The introduction may be performed by those skilled in the art by selecting a suitable transformation method known in the art, and a protein can be produced as the introduced polynucleotides are expressed in the host cell, thereby increasing its activity.

Finally, the method for modification to enhance the activity by a combination of methods 1) to 4) in method 5) may be performed by a combined application of at least one of the following methods: increasing the copy number of the polynucleotide encoding the protein, modifying an expression regulatory sequence such that the expression of the polynucleotide is increased, modifying the polynucleotide sequence on a chromosome, and modifying a foreign polynucleotide exhibiting the activity of the protein or a codon-optimized modified polynucleotide thereof.

As used herein, the term "weakening" of the activity of a protein includes both reduction in activity or having no activity at all, as compared to the endogenous activity thereof.

The weakening of the activity of a protein may be achieved by various methods well known in the art. Examples of the methods include a method of deleting a part or the entirety of a gene encoding the protein on a chromosome, including the case where the activity of the protein is eliminated; a method of replacing the gene encoding the protein on the chromosome with a gene mutated so as to reduce the enzyme activity; a method of introducing a modification into an expression regulatory sequence of the gene encoding the protein on the chromosome; a method of replacing an expression regulatory sequence of the gene encoding the protein with a sequence having a weak activity or no activity (e.g., a method of replacing the gene promoter with a promoter weaker than the endogenous promoter); a method of deleting a part or the entirety of a gene encoding the protein on a chromosome; a method of introducing an antisense oligonucleotide that binds complementarily to the transcript of the gene on the chromosome to inhibit the translation of the mRNA into the protein (e.g., antisense RNA); a method of artificially adding a sequence complementary to the upstream of the SD sequence of the gene encoding the enzyme to form a secondary structure, thereby making the adhesion of ribosome impossible; and a method of reverse transcription engineering (RTE), which adds a promoter to the 3' end of the open reading frame (ORF) of the corresponding sequence so as to be reverse-transcribed, or a combination thereof, but are not particularly limited thereto.

Specifically, the method of deleting a part or the entirety of a gene encoding the protein may be performed by replacing the polynucleotide encoding the endogenous target protein within the chromosome with a polynucleotide having a partially deleted nucleic acid sequence or a marker gene through a vector for chromosomal insertion into microorganisms. In an embodiment, a method for deleting a gene by homologous recombination may be used, but is not limited thereto. Additionally, as used herein, the term "part", although it may vary depending on the kinds of polynucleotide and may be appropriately selected by those skilled in the art, may specifically refer to 1 to 300 nucleotides, more specifically 1 to 100 nucleotides, and even more specifically 1 to 50 nucleotides, but is not particularly limited thereto.

Additionally, the method of modifying an expression regulatory sequence may be performed by inducing a modification in the expression regulatory sequence through deletion, insertion, conservative or non-conservative substitution, or a combination thereof so as to further weaken the activity of the expression regulatory sequence; or by replacing the sequence with a nucleic acid sequence having a weaker activity. The expression regulatory sequence may include a promoter, an operator sequence, a sequence encoding a ribosome-binding domain, and a sequence regulating the termination of transcription and translation, but is not limited thereto.

Further, the method of modifying the gene sequence on the chromosome may be performed by inducing a modification in the gene sequence through deletion, insertion, conservative or non-conservative substitution, or a combination thereof so as to further weaken the activity of the protein; or by replacing the sequence with a gene sequence modified to have a weaker activity or a gene sequence modified to have no activity at all, but is not limited thereto.

Still another aspect of the present disclosure provides a method for producing an ornithine-based product, comprising:

(i) culturing a microorganism producing an ornithine-based product comprising the polypeptide having an ability to export an ornithine-based product or having an enhanced activity thereof in a medium; and (ii) recovering the ornithine-based product from the microorganism or the medium obtained above.

In a specific embodiment, the present disclosure provides a method for producing putrescine, comprising:

(i) culturing a microorganism producing putrescine comprising the polypeptide having an ability to export an ornithine-based product or having an enhanced activity thereof in a medium; and (ii) recovering putrescine from the microorganism or the medium obtained above.

In another specific embodiment, the present disclosure provides a method for producing L-arginine, comprising:

(i) culturing a microorganism producing L-arginine comprising the polypeptide having an ability to export an ornithine-based product or having an enhanced activity thereof in a medium; and (ii) recovering L-arginine from the microorganism or the medium obtained above.

The polypeptide having an ability to export an ornithine-base product and/or the microorganism producing an ornithine-based product are as described above.

In the method above, the culturing of the microorganism may be performed by a known batch culture method, continuous culture method, fed-batch culture method, etc., but is not particularly limited thereto. In particular, with respect to the culture conditions, the pH of the culture may be adjusted to a suitable pH (e.g., pH 5 to 9, specifically pH 6 to 8, and most specifically pH 6.8) using a basic compound (e.g., sodium hydroxide, potassium hydroxide, or ammonia) or an acidic compound (e.g., phosphoric acid or sulfuric acid). Additionally, oxygen or oxygen-containing gas mixture may be injected into the culture in order to maintain an aerobic state. The culture temperature may be maintained at 20° C. to 45° C., specifically at 25° C. to 40° C., and the culturing may be performed for about 10 hours to 160 hours, but the culture is not limited to the above. The putrescine produced by the culture may be secreted in the medium or may remain in the cells.

Additionally, as a carbon source for the culture medium to be used, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but is not limited thereto. As a nitrogen source, nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but is not limited thereto. As a phosphorus source, potassium dihydrogen phosphate, dipotassium hydrogen phosphate, corresponding sodium-containing salts thereof, etc. may be used alone or in combination, but is not limited thereto. In addition, essential growth-promoting materials such as other metal salts (e.g., magnesium sulfate or iron sulfate), amino acids, vitamins, etc. may be contained in the medium.

In the method for recovering the ornithine-based product produced in the culturing step of the present disclosure, the desired products may be collected from the cultured microorganism or medium using an appropriate method known in the art. For example, centrifugation, filtration, anion-exchange chromatography, crystallization, HPLC, etc. may be used, but is not limited thereto. Additionally, the method for recovering the ornithine-based product may further include a purification process using an appropriate method known in the art.

DETAILED DESCRIPTION OF PREFERRED EMBODIMENTS

The present disclosure will be described in more detail through exemplary embodiments. However, these exemplary embodiments are given for illustrative purposes only, and are not intended to limit the scope of the present disclosure.

Example 1

Confirmation of Ability to Export Arginine of Putrescine-Exporting Protein

It has been found that NCgl2522, a gene of *Corynebacterium glutamicum*, has an ability to export putrescine (Korean Patent Application Publication No. 2014-0115244). To this end, the following experiment was conducted to confirm whether NCgl2522 can also export citrulline, proline, and arginine, which can be biosynthesized from ornithine as a starting material, in addition to putrescine.

Specifically, it was confirmed whether NCgl2522 has an ability to export arginine as a representative example, among the products that can be biosynthesized from ornithine as a starting material.

<1-1> Construction of Arginine-Producing Strain-Based Vectors and Strains Having Enhanced NCgl2522 Activity In order to enhance the NCgl2522 activity in the wild-type ATCC21831 strain and KCCM10741P (Korean Patent No. 10-0791659) having an arginine-producing ability, the CJ7 promoter (WO 2006/065095 A) was introduced to the upstream of the initiation codon of NCgl2522 within the chromosome.

A homologous recombinant fragment, which includes the CJ7 promoter disclosed in WO 2006/065095 A and in which both ends of the promoter have the original NCgl2522 sequence on the chromosome, was obtained. Specifically, the 5'-end region of the CJ7 promoter was obtained by performing PCR using a primer pair of SEQ ID NOS: 17 and 18 shown in Table 1, based on the genomic DNA of the *Corynebacterium glutamicum* ATCC21831 or KCCM10741P as a template. In particular, the PCR reaction was performed by repeating 30 cycles of denaturation at 94° C. for 30 seconds, annealing at 55° C. for 30 seconds, and extension at 72° C. for 30 seconds. Additionally, the CJ7 promoter region was obtained by performing PCR under the same conditions using a primer pair of SEQ ID NOS: 19 and 20 shown in Table 1, and the 3'-end region of the CJ7 promoter was obtained by performing PCR using a primer pair of SEQ ID NOS: 20 and 21 shown in Table 1 under the same conditions, based on the genomic DNA of the *Coryne-*

*bacterium glutamicum* ATCC21831 or KCCM10741P as a template. The primers used in the substitution of promoters are shown in Table 1 below.

TABLE 1

| Primers | Sequence (5'->3') |
|---|---|
| NCgl2522-L5 (SEQ ID NO: 17) | TGCAGGTCGACTCTAGA GTTCTGCGTAGCTGTGTGCC |
| NCgl2522-L3 (SEQ ID NO: 18) | GATGTTTCT GGATCGTAACTGTAACGAATGG |
| CJ7-F (SEQ ID NO: 19) | AGAAACATCCCAGCGCTACTAATA |
| CJ7-R (SEQ ID NO: 20) | AGTGTTTCCTTTCGTTGGGTACG |
| NCgl2522-R5 (SEQ ID NO: 21) | CAACGAAAGGAAACACT ATGATTTCAGAAACTTTGCAGGCG |
| NCgl2522-R3 (SEQ ID NO: 22) | TCGGTACCCGGGGATCC CACAAAAAGCGTAGCGATCAACG |

Each of the PCR products obtained above was subjected to fusion cloning into the pDZ vector treated with BamHI and XbaI. The fusion cloning was performed at 50° C. for 10 minutes using the In-Fusion® HD Cloning Kit (Clontech Laboratories, Inc.), and the thus-obtained plasmids were named pDZ-P(CJ7)-NCgl2522-21831 and pDZ-P(CJ7)-NCgl2522-10741P, respectively.

The plasmids pDZ-P(CJ7)-NCgl2522-21831 and pDZ-P(CJ7)-NCgl2522-10741P prepared above were respectively introduced into ATCC21831 and KCCM10741P, which are arginine-producing strains, via electroporation to obtain transformants, and the thus-obtained transformants were plated on BHIS plate media (37 g/L of Braine heart infusion, 91 g/L of sorbitol, and 2% agar) containing kanamycin (25 μg/mL) and X-gal (5-bromo-4-chloro-3-indolin-D-galactoside) and cultured to form colonies. Among the thus-formed colonies, the strains introduced with the plasmid pDZ-P(CJ7)-NCgl2522-21831 or pDZ-P(CJ7)-NCgl2522-10741P were selected.

The selected strains were cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from $10^{-4}$ to $10^{-10}$, plated on solid media containing X-gal, and cultured to form colonies. Among the thus-formed colonies, white colonies which appeared at a relatively low rate were selected, thereby finally selecting the strains, in which the promoter of the NCgl2522 gene was substituted with the CJ7 promoter by a secondary crossover. The finally selected strains were subjected to PCR using a primer pair of SEQ ID NOS: 19 and 22 shown in Table 1, and the thus-obtained products were applied to sequencing. As a result, it was confirmed that the CJ7 promoter was introduced into the upstream of the initiation codon of NCgl2522 within the chromosome. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named ATCC21831_Pcj7 Ncgl2522 and KCCM10741P_Pcj7 NCgl2522, respectively.
<1-2> Confirmation of Arginine-Producing Ability of Arginine-Producing Strain-Based Strains Having Enhanced NCgl2522 Activity In order to confirm the effect of the NCgl2522 gene on the ability to export arginine, one of the ornithine-based products, the arginine-producing ability was compared among the modified strains of *Corynebacterium glutamicum* ATCC21831_Pcj7 Ncgl2522 and KCCM10741P_Pcj7 NCgl2522 prepared in Example 1 above.

As the control groups, *Corynebacterium glutamicum* ATCC21831 and KCCM10741P, which are the parent strains, were used, and one platinum loop of each strain was inoculated into a 250-mL corner-baffled flask containing 25 mL1 of production media [6% glucose, 3% ammonium sulfate, 0.1% monopotassium phosphate, 0.2% magnesium sulfate heptahydrate, 1.5% corn steep liquor (CSL), 1% NaCl, 0.5% yeast extract, and 100 μg/L of biotin at pH7.2] and cultured at 30° C. at a rate of 200 rpm for 48 hours to produce arginine. After completion of the culture, the arginine production was measured by HPLC. The results are shown in Table 2 below.

TABLE 2

| Strains | OD | Arginine Concentration (g/L) | Ornithine Concentration (g/L) | Arginine Fold (%) |
|---|---|---|---|---|
| KCCM10741P | 91 | 3.0 | 0.3 | 100 |
| KCCM10741P_Pcj7 Ncgl2522 | 72 | 3.6 | 0.4 | 120 |
| ATCC21831 | 102 | 4.2 | 0.3 | 100 |
| ATCC21831_Pcj7 Ncgl2522 | 86 | 4.8 | 0.4 | 114 |

As shown in Table 2, when the promoter of the NCgl2522 gene in KCCM10741P and ATCC21831 was enhanced by substitution with the CJ7 promoter, the modified strains of *Corynebacterium glutamicum* showed an increase in the arginine production by 20% and 14% as compared to the parent strains, respectively. Additionally, it was confirmed that the concentration of ornithine, a reactant before conversion to arginine, was also increased in the modified strains as compared to the parent strains.

Based on these findings, it was confirmed that the NCgl2522 gene is not only a gene for exporting putrescine, but also has an ability to export products including ornithine which are biosynthesized from ornithine as a starting material. Additionally, it can be interpreted from the above results that the NCgl2522 gene and the variants of the present disclosure can be very useful in the production of ornithine-based products using biomass.

Example 2

Construction of Library of Gene Variants Encoding Putrescine-Exporting Protein and Establishment of Effective Modification In order to increase the activity of the ornithine-based product-exporting protein, the present inventors constructed variants for NCgl2522 (Korea Patent No. 10-1607741), a gene encoding a putrescine-exporting protein.

Specifically, in order to construct a library of the NCgl2522 gene variants, a random mutagenesis PCR (JENA error-prone PCR) was performed using a specific primer pair of SEQ ID NOS: 7 and 8 excluding the initiation codon of ORF of the NCgl2522 gene, shown in Table 3, based on the genomic DNA of *Corynebacterium glutamicum* ATCC13032 as a template.

TABLE 3

| Primer | Sequence (5'->3') |
| --- | --- |
| 13032-putE-EF-FX (SEQ ID NO: 7) | CCGGGGATCCTCTAGA ACTTCAGAAACCTTACAGGC |
| 13032-putE-EF-RX (SEQ ID NO: 8) | GCAGGTCGACTCTAGA CTAGTGCGCATTATTGGCTC |

The thus-prepared mutant gene fragments were subjected to fusion cloning into the pDZ vector cleaved with XbaI. The fusion cloning was performed at 50° C. for 10 minutes using the In-Fusion® HD Cloning Kit (Clontech Laboratories, Inc.), thereby completing the construction of plasmid libraries of pDZ-N2522 variants.

The thus-constructed recombinant plasmid libraries were screened via high throughput screening (HTS). In particular, the platform strain used for screening was KCCM11240P, which is a *Corynebacterium glutamicum*-derived recombinant microorganism capable of producing putrescine (Korean Patent No. 10-1493585).

Specifically, in order to obtain variants with an improved activity for exporting putrescine, the thus-constructed plasmid libraries were introduced into KCCM11240P via electroporation to obtain transformants, and the thus-obtained transformants were plated on BHIS plate media (37 g/L of Braine heart infusion, 91 g/L of sorbitol, and 2% agar) containing kanamycin (25 μg/mL) and X-gal (5-bromo-4-chloro-3-indolin-D-galactoside) and cultured to form colonies. Among the thus-formed colonies, the strains introduced with the plasmid pDZ-N2522 variant libraries were selected.

The selected strains were cultured by shaking in a 96 deep well plate along with titer media (2 g/L of glucose, 0.4 g/L of $MgSO_4 \cdot 7H_2O$, 0.8 g/L of $MgCl_2$, 1 g/L of $KH_2PO_4$, 4 g/L of $(NH_4)_2SO_4$, 0.48 g/L of soybean protein hydrolysate, 0.01 g/L of $MnSO_4 \cdot 7H_2O$, 200 μg/L of thiamine HCl, 200 μg/L of biotin, 0.01 g/L of $FeSO_4 \cdot 7H_2O$, 1 mM arginine, and 25 μg/mL of kanamycin at pH 7.2), and the concentration of putrescine produced in each culture was measured, and then one transformant with the greatest increase in putrescine productivity compared to the control group was selected. Subsequently, it was confirmed as to which modification was induced in the amino acid sequence of the NCgl2522 protein for the selected transformant. The sequence of the Ncgl2522 variant was confirmed as follows: a homologous recombinant fragment was obtained by performing colony PCR using a primer pair of SEQ ID NOS: 7 and 8, based on the transformant including the corresponding variants, followed by applying the product to genome sequencing using a primer of SEQ ID NO: 7. In particular, the PCR reaction was performed by repeating 30 cycles of denaturation at 95° C. for 30 seconds, annealing at 55° C. for 30 seconds, and extension at 72° C. for 1 minute.

As a result, it was confirmed that the NCgl2522 variant selected therefrom was modified such that the glycine (Gly), which is the amino acid residue at position 77 from the N-terminus of the NCgl2522 amino acid sequence (SEQ ID NO: 1) of *Corynebacterium glutamicum* ATCC13032, was substituted with alanine (Ala), and was named NCgl2522_G77A (SEQ ID NO: 3).

Example 3

Establishment of Various Variants in which Amino Acid Residue at Position 77 of Gene Encoding Putrescine-Exporting Protein is Substituted Based on the NCgl2522_G77A variant prepared in Example 2, the present inventors realized that the amino acid residue at position 77 from the N-terminus is important for the activity of the NCgl2522 protein. Accordingly, various variants in which the amino acid residue at position 77 of the NCgl2522 protein was substituted with other amino acid residues were prepared.

Specifically, a homologous recombinant fragment was obtained using a specific primer pair of SEQ ID NOS: 7 and 8 excluding the initiation codon of ORF of NCgl2522 gene, based on the genomic DNA of *Corynebacterium glutamicum* ATCC13032 as a template. In particular, the PCR reaction was performed by repeating 30 cycles of denaturation at 95° C. for 30 seconds, annealing at 55° C. for 30 seconds, and extension at 72° C. for 1 minute.

Subsequently, the PCR product obtained above was subjected to fusion cloning into the pDZ vector treated with XbaI. The fusion cloning was performed using the In-Fusion® HD Cloning Kit (Clontech Laboratories, Inc.), and the thus-obtained plasmid was named pDZ-NCgl2522_G77.

Then, in order to induce a random mutagenesis on the amino acid residue at position 77 of NCgl2522, a plasmid library for the pDZ-NCgl2522_G77 variant was completed by performing PCR using a primer pair of SEQ ID NOS: 9 and 10 shown in Table 4, based on the plasmid pDZ-NCgl2522_G77 constructed above as a template. In particular, the PCR reaction was performed by repeating 25 cycles of denaturation at 95° C. for 30 seconds, annealing at 55° C. for 30 seconds, and extension at 72° C. for 5 minutes.

Table 4

| Primer | Sequence (5'->3') |
| --- | --- |
| SM_putE_G77-F (SEQ ID NO: 9) | TGGGGTTCCGTGNNKATTCTTGGCGCT |
| SM_putE_G77-R (SEQ ID NO: 10) | AGCGCCAAGAATMNNCACGGAACCCCA |

The thus-constructed recombinant plasmid libraries were screened via high throughput screening (HTS). In particular, the platform strain used for screening was KCCM11240P, which is a *Corynebacterium glutamicum*-derived recombinant microorganism capable of producing putrescine.

The constructed plasmid libraries were introduced into KCCM11240P via electroporation to obtain transformants, and the strains introduced with the plasmid pDZ-NCgl2522_G77 variant were selected in the same manner as in Example 2. Two transformants with the greatest increase in putrescine productivity compared to the control group were selected, and it was confirmed as to which modification was induced in the amino acid sequence of the NCgl2522 protein for each transformant, in the same manner as in Example 2.

As a result, in addition to the NCgl2522 G77A (ATCC13032) variant (SEQ ID NO: 3), in which glycine, the amino acid residue at position 77 from the N-terminus of the amino acid sequence (SEQ ID NO: 1) of NCgl2522 of *Corynebacterium glutamicum* ATCC13032, was substituted with alanine, the variant in which the glycine was substituted with arginine was confirmed and was named NCgl2522_G77R (ATCC13032) (SEQ ID NO: 4).

Additionally, in order to confirm whether the effect of increasing putrescine productivity due to the modification can be applied to NCgl2522 proteins derived from different strains, various variants, in which the amino acid residue at position 77 of the NCgl2522 protein derived from *Corynebacterium glutamicum* ATCC13869 was substituted with other amino acid residues, were constructed.

Specifically, a homologous recombinant fragment was obtained using a specific primer pair of SEQ ID NOS: 7 and 8 excluding the initiation codon of ORF of NCgl2522 gene, based on the genomic DNA of *Corynebacterium glutamicum* ATCC13869 as a template. In particular, the PCR reaction was performed by repeating 30 cycles of denaturation at 95° C. for 30 seconds, annealing at 55° C. for 30 seconds, and extension at 72° C. for 30 seconds.

The PCR product obtained above was subjected to fusion cloning into the pDZ vector treated with XbaI. The fusion cloning was performed using the In-Fusion® HD Cloning Kit (Clontech Laboratories, Inc.), and the thus-obtained plasmid was named pDZ-13869-NCgl2522_G77.

Then, in order to induce a random mutagenesis on the amino acid residue at position 77 of NCgl2522, a plasmid library for the pDZ-13869-NCgl2522_G77 variant was completed by performing PCR using a primer pair of SEQ ID NOS: 9 and 10 shown in Table 4, based on the plasmid pDZ-13869-NCgl2522_G77 constructed above as a template. In particular, the PCR reaction was performed by repeating 25 cycles of denaturation at 95° C. for 30 seconds, annealing at 55° C. for 30 seconds, and extension at 72° C. for 5 minutes.

Subsequently, the thus-constructed recombinant plasmid libraries were screened via high throughput screening (HTS). In particular, the platform strain used for screening was DAB12-b, which is a *Corynebacterium glutamicum*-derived recombinant microorganism capable of producing putrescine. Then, the constructed plasmid libraries were introduced into DAB12-b via electroporation to obtain transformants, and the strains introduced with the plasmid pDZ-13869-NCgl2522_G77 variant were selected in the same manner as in Example 2.

As a result, two variants, in which the amino acid residue at position 77 from the N-terminus of the NCgl2522 amino acid sequence (SEQ ID NO: 2) of *Corynebacterium glutamicum* ATCC13869 was substituted, were selected as the strains with the greatest putrescine production, as the NCgl2522 variants of *Corynebacterium glutamicum* ATCC13032. Among them, the variant in which glycine, the amino acid residue at position 77, was substituted with alanine was named NCgl2522_G77A (ATCC13869) (SEQ ID NO: 5), and the variant in which glycine, the amino acid residue at position 77, was substituted with arginine was named NCgl2522_G77R (ATCC13869) (SEQ ID NO: 6).

Example 4

Construction of NCgl2522 Variant Strains and Confirmation of Putrescine-Producing Ability Thereof <4-1> Construction of NCgl2522 Variant Strains from ATCC13032-based Putrescine-Producing Strain In order to increase the ability to export putrescine of the putrescine-producing strain, NCgl2522_G77A and NCgl2522_G77R, which are variants of the NCgl2522 gene, were respectively introduced into the chromosome of the *Corynebacterium glutamicum* ATCC13032-based putrescine-producing strain.

Specifically, a homologous recombinant fragment having a modified sequence of NCgl2522_G77A was obtained by performing PCR using primer pairs of SEQ ID NOS: 11 and 14, and SEQ ID NOS: 12 and 13, based on the genomic DNA of *Corynebacterium glutamicum* ATCC13032 as a template, and a homologous recombinant fragment having a modified sequence of NCgl2522_G77R was obtained using primer pairs of SEQ ID NOS: 11 and 16, and SEQ ID NOS: 12 and 15, based on the genomic DNA of *Corynebacterium glutamicum* ATCC13032 as a template. In particular, the PCR reaction was performed by repeating 30 cycles of denaturation at 95° C. for 30 seconds, annealing at 55° C. for 30 seconds, and extension at 72° C. for 30 seconds.

TABLE 5

| Primer | Sequence (5'->3') |
|---|---|
| pDC-Pself-putE-up-FX (SEQ ID NO: 11) | CCGGGGATCCTCTAGA CCTCTAAGCGCCTCAAAG |
| pDC-putE-up-RX (SEQ ID NO: 12) | GCAGGTCGACTCTAGA GATTCGCGATATTGGCCG |
| putE_G77A-F (SEQ ID NO: 13) | CCGGCACTTTGGCTGACAAAATCG |
| putE_G77A-R (SEQ ID NO: 14) | CGATTTTGTCAGCCAAAGTGCCGG |
| putE_G77R-F (SEQ ID NO: 15) | CCGGCACTTTGCGTGACAAAATCG |
| putE_G77R-R (SEQ ID NO: 16) | CGATTTTGTCACGCAAAGTGCCGG |

Each of the PCR products obtained above was subjected to fusion cloning into the pDZ vector treated with XbaI. The fusion cloning was performed using the In-Fusion® HD Cloning Kit (Clontech Laboratories, Inc.), and the thus-obtained plasmids were named pDZ-NCgl2522_G77A and pDZ-NCgl2522_G77R, respectively.

The plasmids pDZ-NCgl2522_G77A and pDZ-NCgl2522_G77R prepared above were respectively introduced into KCCM11240P (Korean Patent Application Publication No. 2013-0082478), which is a *Corynebacterium glutamicum* ATCC13032-based putrescine-producing strain, via electroporation to obtain transformants, and the thus-obtained transformants were plated on BHIS plate media (37 g/L of Braine heart infusion, 91 g/L of sorbitol, and 2% agar) containing kanamycin (25 μg/mL) and X-gal (5-bromo-4-chloro-3-indolin-D-galactoside) and cultured to form colonies. Among the thus-formed colonies, the strains introduced with the plasmids pDZpDZ-NCgl2522_G77A or pDZ-NCgl2522_G77R were selected.

The selected strains were cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from $10^{-4}$ to $10^{-10}$, plated on solid media containing X-gal, and cultured to form colonies. Among the thus-formed colonies, white colonies which appeared at a relatively low rate were selected, thereby finally selecting the strains, in which the NCgl2522 gene was substituted with the NCgl2522_G77A or NCgl2522_G77R variant by a secondary crossover. The finally selected strains were subjected to PCR using a primer pair of SEQ ID NOS: 11 and 12, and the thus-obtained products were applied to sequencing to confirm the substitution with the variants. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named KCCM11240P NCgl2522_G77A and KCCM11240P NCgl2522_G77R, respectively.

<4-2> Construction of NCgl2522 Variant Strains from ATCC13869-based Putrescine-Producing Strain DAB12-a ΔNCgl1469 (Korean Patent Application Publication No. 2013-0082478), which is a *Corynebacterium*

*glutamicum* ATCC13869-based putrescine-producing strain, was named DAB12-b. To this end, in order to increase the ability to export putrescine of the putrescine-producing strain, NCgl2522_G77A and NCgl2522_G77R, which are variants of NCgl2522 gene, were respectively introduced into the chromosome of the DAB12-b strain.

Specifically, a homologous recombinant fragment having a modified sequence of NCgl2522_G77A was obtained by performing PCR using primer pairs of SEQ ID NOS: 11 and 14, and SEQ ID NOS: 12 and 13 shown in Table 5, based on the genomic DNA of *Corynebacterium glutamicum* ATCC13869 as a template, and a homologous recombinant fragment having a modified sequence of NCgl2522_G77R was obtained by performing PCR using primer pairs of SEQ ID NOS: 11 and 16, and SEQ ID NOS: 12 and 15 shown in Table 5, based on the genomic DNA of *Corynebacterium glutamicum* ATCC13869 as a template. In particular, the PCR reaction was performed by repeating 30 cycles of denaturation at 95° C. for 30 seconds, annealing at 55° C. for 30 seconds, and extension at 72° C. for 30 seconds.

Each of the PCR products obtained above was subjected to fusion cloning into the pDZ vector treated with XbaI. The fusion cloning was performed using the In-Fusion® HD Cloning Kit (Clontech Laboratories, Inc.), and the thus-obtained plasmids were named pDZ-NCgl2522_G77A-2 and pDZ-NCgl2522_G77R-2, respectively.

The plasmids pDZ-NCgl2522_G77A-2 and pDZ-NCgl2522_G77R-2 prepared above were respectively introduced into DAB12-b via electroporation to obtain transformants, and the thus-obtained transformants were plated on BHIS plate media (37 g/L of Braine heart infusion, 91 g/L of sorbitol, and 2% agar) containing kanamycin (25 μg/mL) and X-gal (5-bromo-4-chloro-3-indolin-D-galactoside) and cultured to form colonies. Among the thus-formed colonies, the strains introduced with the plasmid pDZ-NCgl2522_G77A-2 or pDZ-NCgl2522_G77R-2 were selected.

The selected strains were cultured with shaking (30° C., 8 hours) in CM media (10 g/L of glucose, 10 g/L of polypeptone, 5 g/L of yeast extract, 5 g/L of beef extract, 2.5 g/L of NaCl, and 2 g/L of urea at pH 6.8) and sequentially diluted from $10^{-4}$ to $10^{-10}$, plated on solid media containing X-gal, and cultured to form colonies. Among the thus-formed colonies, white colonies which appeared at a relatively low rate were selected, thereby finally selecting the strains, in which the NCgl2522 gene was substituted with the NCgl2522_G77A or NCgl2522_G77R variant by a secondary crossover. The finally selected strains were subjected to PCR using a primer pair of SEQ ID NOS: 11 and 12, and the thus-obtained products were applied to sequencing to confirm the substitution with the variants. In particular, the PCR reaction was performed by repeating 30 cycles of denaturation at 95° C. for 30 seconds, annealing at 55° C. for 30 seconds, and extension at 72° C. for 1 minute.

The thus-selected modified strains of *Corynebacterium glutamicum* were named DAB12-b NCgl2522_G77A and DAB12-b NCgl2522_G77R, respectively.

<4-3> Evaluation of Putrescine-Producing Ability of Strains Introduced with NCgl2522 Variants In order to confirm the effect of NCgl2522 variants on putrescine production when the variants of the NCgl2522 gene, which increases the ability to export putrescine, were introduced into the putrescine-producing strains, the putrescine-producing ability was compared among the modified strains of *Corynebacterium glutamicum* prepared in Examples 4-1 and 4-2.

Specifically, the modified strains of *Corynebacterium glutamicum* (KCCM11240P NCgl2522_G77A and DAB12-b NCgl2522_G77R) and two kinds of parent strains (KCCM11240P and DAB12-b) were respectively plated on 1 mM arginine-containing CM plate media (1% glucose, 1% polypeptone, 0.5% yeast extract, 0.5% beef extract, 0.25% NaCl, 0.2% urea, 100 μL of 50% NaOH, and 2% agar at pH 6.8, based on 1 L), and cultured at 30° C. for 24 hours. About one platinum loop of each strain cultured therefrom was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, 100 μg of biotin, 3 mg of thiamine HCl, 3 mg of calcium-pantothenic acid, 3 mg of nicotinamide, and 5% $CaCO_3$, based on 1 L), and cultured with shaking at 30° C. at a rate of 200 rpm for 50 hours. During culturing of all strains, 1 mM arginine was added to the media. After completion of the culture, the concentration of putrescine produced in each culture was measured, and the results are shown in Table 6 below.

TABLE 6

| Name of Strains | Putrescine (g/L) | Productivity (g/L/h) | Fold (%) |
| --- | --- | --- | --- |
| KCCM11240P | 5.8 | 0.116 | 100 |
| KCCM11240P NCgl2522_G77A | 6.8 | 0.136 | 117 |
| KCCM11240P NCgl2522_G77R | 6.3 | 0.126 | 109 |
| DAB12-b | 6.5 | 0.129 | 100 |
| DAB12-b NCgl2522_G77A | 7.3 | 0.146 | 113 |
| DAB12-b NCgl2522_G77R | 7.1 | 0.142 | 110 |

As shown in Table 6 above, when the NCgl2522_G77A and NCgl2522_G77R variants were respectively introduced into KCCM11240P and DAB12-b, the modified strains of *Corynebacterium glutamicum* introduced with the variants showed an increase in the putrescine production and productivity by 7% to 13% as compared to the parent strains, respectively. In particular, the productivity represents the putrescine production per hour for each transformant, and was expressed in g/L/h.

Example 5

Introduction of NCgl2522 Variants into Putrescine-Producing Strains with Improved Ability to Export Putrescine and Confirmation of Putrescine-Producing Ability Thereof <5-1> Construction of Strains by Introducing NCgl2522 Variants into Strains with Improved Ability to Export Putrescine In order to confirm the effect of the variants of the NCgl2522 gene, NCgl2522_G77A and NCgl2522_G77R were respectively introduced into the chromosome of KCCM11240P P(CJ7)-NCgl2522 (Korean Patent Application Publication No. 2014-0115244), which is a *Corynebacterium glutamicum* ATCC13032-based putrescine-producing strain with an increased ability to export putrescine.

Specifically, pDZ-NCgl2522_G77A and pDZ-NCgl2522_G77R prepared in Example 4-1 were respectively transformed into KCCM11240P P(CJ7)-NCgl2522 in the same manner as in Example 4-1, and thus it was confirmed that the NCgl2522 gene was substituted with the variants within the chromosome thereof. The selected modified strains of *Corynebacterium glutamicum* were named KCCM11240P P(CJ7)-NCgl2522 NCgl2522_G77A and KCCM11240P P(CJ7)-NCgl2522 NCgl2522_G77R, respectively.

<5-2> Evaluation of Putrescine-Producing Ability of Strains Prepared by Introducing NCgl2522 Variants into Strain with Improved Ability to Export Putrescine In order to confirm the effect of the NCgl2522 variants on the Corynebacterium glutamicum producing strains with an improved ability to export putrescine, the putrescine-producing ability was compared among the modified strains of Corynebacterium glutamicum prepared in Example 5-1 and the parent strain.

Specifically, the modified strains of Corynebacterium glutamicum (KCCM11240P P(CJ7)-NCgl2522 NCgl2522_G77A and KCCM11240P P(CJ7)-NCgl2522 NCgl2522_G77R) and the parent strain (KCCM11240P P(CJ7)-NCgl2522) were respectively plated on 1 mM arginine-containing CM plate media (1% glucose, 1% polypeptone, 0.5% yeast extract, 0.5% beef extract, 0.25% NaCl, 0.2% urea, 100 μL of 50% NaOH, and 2% agar at pH 6.8, based on 1 L), and cultured at 30° C. for 24 hours. About one platinum loop of each strain cultured therefrom was inoculated into 25 mL of titer media (8% glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, 100 μg of biotin, 3 mg of thiamine HCl, 3 mg of calcium-pantothenic acid, 3 mg of nicotinamide, and 5% $CaCO_3$, based on 1 L), and cultured with shaking at 30° C. at a rate of 200 rpm for 50 hours. During culturing of all strains, 1 mM arginine was added to the media. After completion of the culture, the concentration of putrescine produced in each culture was measured, and the results are shown in Table 7 below

TABLE 7

| Name of Strains | Putrescine (g/L) | Productivity (g/L/h) | Fold (%) |
|---|---|---|---|
| KCCM11240P P(CJ7)-NCgl2522 | 6.9 | 0.138 | 100 |
| KCCM11240P P(CJ7)-NCgl2522 NCgl2522_G77A | 7.6 | 0.152 | 110 |
| KCCM11240P P(CJ7)-NCgl2522 NCgl2522_G77R | 7.5 | 0.150 | 109 |

As shown in Table 7 above, when the NCgl2522_G77A and NCgl2522_G77R variants were respectively introduced into KCCM11240P P(CJ7)-NCgl2522 with an improved ability to export putrescine, the modified strains of Corynebacterium glutamicum showed an increase in the putrescine production and productivity by 9% to 10% as compared to the parent strain, which already showed an improved ability to export putrescine. In particular, the productivity represents the putrescine production per hour for each transformant, and was expressed in g/L/h.

Example 6

Introduction of NCgl2522 Variants into Arginine-Producing Strains and Confirmation of Arginine-Producing Ability Thereof <6-1> Construction of Strains by Introducing NCgl2522 Variants into Arginine-Producing Strains In order to increase the ability to export L-arginine of the L-arginine-producing strains, NCgl2522_G77A and NCgl2522_G77R, which are variants of the NCgl2522 gene, were respectively introduced into the chromosomes of Corynebacterium glutamicum ATCC21831 and KCCM10741P (Korean Patent No. 10-0791659).

Specifically, the strains, in which the NCgl2522 gene was substituted with NCgl2522_G77A and NCgl2522_G77R variants, were finally selected in the same manner as in Example 4-2. The modified strains of Corynebacterium glutamicum selected therefrom were named KCCM10741P NCgl2522_G77A, KCCM10741P NCgl2522_G77R, ATCC21831_Pcj7 Ncgl2522_G77A, and ATCC21831_Pcj7 Ncgl2522_G77R, respectively.

<6-2> Evaluation of L-arginine-Producing Ability of Strains Introduced with NCgl2522 Variants In order to confirm the effect of the NCgl2522 variants on L-arginine production when the variants of the NCgl2522 gene, which increases the ability to export L-arginine, were introduced into the L-arginine-producing strains, the L-arginine-producing ability was compared among the modified strains of Corynebacterium glutamicum prepared in Example 6-1.

In particular, as the control groups, the Corynebacterium glutamicum KCCM10741P and ATCC21831, which are the parent strains, and KCCM10741P_Pcj7 Ncgl2522 and ATCC21831_Pcj7 Ncgl2522, which were prepared in Example 1, were used. One platinum loop of each strain was inoculated into a 250 mL corner-baffled flask containing 25 mL of production media [6% glucose, 3% ammonium sulfate, 0.1% monopotassium phosphate, 0.2% magnesium sulfate heptahydrate, 1.5% corn steep liquor (CSL), 1% NaCl, 0.5% yeast extract, and 100 μg/L of biotin at pH7.2] and cultured with shaking at 30° C. at a rate of 200 rpm for 48 hours to produce L-arginine. After completion of the culture, the L-arginine production was measured by HPLC. The results are shown in Table 8 below.

TABLE 8

| Strains | OD | Arginine Concentration (g/L) | Ornithine Concentration (g/L) | Arginine Fold (%) |
|---|---|---|---|---|
| KCCM10741P | 91 | 3.0 | 0.3 | 100 |
| KCCM10741P_Pcj7 Ncgl2522 | 72 | 3.6 | 0.4 | 120 |
| KCCM10741P_Pcj7 Ncgl2522_G77A | 69 | 4.1 | 0.5 | 136.7 |
| KCCM10741P_Pcj7 Ncgl2522_G77R | 70 | 4.2 | 0.5 | 140 |
| ATCC21831 | 102 | 4.2 | 0.3 | 100 |
| ATCC21831_Pcj7 Ncgl2522 | 86 | 4.8 | 0.4 | 114 |
| ATCC21831_Pcj7 Ncgl2522_G77A | 86 | 5.4 | 0.5 | 128.6 |
| ATCC21831_Pcj7 Ncgl2522_G77R | 88 | 5.3 | 0.6 | 126.2 |

As shown in Table 8, when the pNCgl2522_G77A and NCgl2522_G77R variants were respectively introduced into KCCM10741P and ATCC21831, all of the modified strains of Corynebacterium glutamicum introduced with the variants showed an increase in the L-arginine production by 26% and 40% as compared to the parent strains.

Additionally, it was confirmed that the concentration of L-ornithine, which was exported after conversion into L-arginine, also increased when the variants were introduced. Based on these findings, it can be interpreted that the modified strains of Corynebacterium glutamicum may also export products biosynthesized from ornithine as a starting material.

In conclusion, the present inventors have confirmed that the amino acid residue at position 77 from the N-terminus plays a key role in the ability to export ornithine-based products in NCgl2522, a putrescine-exporting protein. In particular, when the amino acid at position 77 was substituted with other amino acid residues, it was found that the production of the ornithine-based products was increased in the strains introduced with the variants. Accordingly, the variants of the present disclosure can be applied to a method for producing ornithine-based products using microorganisms to further improve the production thereof, and thus can be very useful for the production of ornithine-based products using biomass.

In the present disclosure, NCgl2522_G77A, a variant of NCgl2522 gene, was introduced into the chromosome of the *Corynebacterium glutamicum* ATCC13032-based putrescine-producing strain, and as a result, it was confirmed that putrescine could be produced with high yield and high productivity in the *Corynebacterium glutamicum* strain introduced with the variant. Accordingly, the strain was named KCCM11240P NCgl2522_G77A and deposited at the Korean Culture Center of Microorganisms (KCCM), an International Depositary Authority, under Budapest Treaty on Sep. 1, 2016 with Accession No. KCCM11886P.

One of ordinary skill in the art will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: CJ CheilJedang Corporation
CJ CHEILJEDANG CENTER,
330, DONGHO-RO,
JUNG-GU, SEOUL 100-400,
REPUBLIC OF KOREA RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM ||
|---|---|
| Identification reference given by the DEPOSITOR: *Corynebacterium glutamicum* CC01-1411 | Accession number given by the INTERNATIONAL DEPOSITARY AUTHORITY: KCCM11886P |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on September. 01. 2016. (date of the original deposit)¹ |

| IV. INTERNATIONAL DEPOSITARY AUTHORITY ||
|---|---|
| Name: Korean Culture Center of Microorganisms <br><br> Address: Yurim B/D <br> 45, Hongjenae-2ga-gil <br> Seodaemun-gu <br> SEOUL 120-861 <br> Republic of Korea | Signature(s) of person(s) having the power to represent the International Depositary Authority or of authorized official(s): <br><br> OFFICIAL SEAL <br><br> Date: September. 01. 2016. |

¹ Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4 Sole page

The invention claimed is:

1. A polypeptide comprising the amino acid sequence of SEQ ID NO: 3, SEQ ID NO:4, SEQ ID NO: 5, or SEQ ID NO: 6, and has export activity of at least one ornithine-based product selected from the group consisting of putrescine, arginine, ornithine, citrulline and proline.

2. The polypeptide of claim 1, wherein the polypeptide consists of the amino acid sequence of SEQ ID NO: 3, SEQ ID NO:4, SEQ ID NO: 5, or SEQ ID NO: 6.

3. A polynucleotide comprising a nucleotide sequence encoding the polypeptide of claim 1.

4. A vector comprising the polynucleotide of claim 3.

5. A modified microorganism of the genus Corynebacterium, wherein the microorganism produces at least one ornithine-based product selected from the group consisting of putrescine, arginine, ornithine, citrulline and proline, and recombinantly expresses the polypeptide of claim 1.

6. The modified microorganism of claim 5, wherein the microorganism is Corynebacterium glutamicum.

7. The modified microorganism of claim 5, wherein the microorganism further recombinantly expresses an ornithine decarboxylase (ODC).

8. The modified microorganism of claim 5, wherein a gene encoding at least one polypeptide selected from the group consisting of ornithine carbamoyltransferase (ArgF) and putrescine acetyltransferase is inactivated or reduced.

9. The modified microorganism of claim 5, wherein the modified microorganism (i) recombinantly expresses or (ii) shows an enhanced activity compared with the endogenous activity of at least one polypeptide selected from the group consisting of acetyl gamma glutamyl phosphate reductase (ArgC), acetylglutamate synthase or ornithine acetyltransferase (argJ), acetylglutamate kinase (ArgB), and acetylornithine aminotransferase (ArgD), wherein the (ii) enhancement of the activity is 1) increasing copy number of the polynucleotide encoding the polypeptide, 2) modifying expression regulatory sequence such that the expression of the polynucleotide is increased, 3) modifying the polynucleotide sequence on a chromosome such that the activity of the polypeptide is enhanced, 4) introducing a foreign polynucleotide exhibiting the activity of the polypeptide or a modified polynucleotide in which the codons of the above polynucleotide have been optimized, or 5) a combination thereof.

10. The modified microorganism of claim 5, wherein the microorganism (i) recombinantly expresses or (ii) shows an increased activity compared with the endogenous activity of at least one polypeptide selected from the group consisting of ornithine carbamoyltransfrase (ArgF), argininosuccinate synthase (argG), argininosuccinate lyase (argH), aspartate ammonia lyase (AAL) and aspartate aminotransferase (AST), wherein the (ii) enhancement of the activity is 1) increasing copy number of the polynucleotide encoding the polypeptide, 2) modifying expression regulatory sequence such that the expression of the polynucleotide is increased, 3) modifying the polynucleotide sequence on a chromosome such that the activity of the polypeptide is enhanced, 4) introducing a foreign polynucleotide exhibiting the activity of the polypeptide or a modified polynucleotide in which the codons of the above polynucleotide have been optimized, or 5) a combination thereof.

11. A method for producing at least one ornithine-based product selected from the group consisting of putrescine, arginine, ornithine, citrulline and proline, comprising:

(i) culturing the microorganism of claim 6 in a medium; and (ii) recovering the at least one ornithine-based product from the microorganism or the medium.

12. A modified microorganism of the genus *Corynebacterium* wherein the microorganism produces putrescine and recombinantly expresses the polypeptide of claim 1, and wherein the putrescine producing ability of the microorganism is enhanced compared to the *Corynebacterium* microorganism that does not express the polypeptide of claim 1.

13. The modified microorganism of claim 12, wherein the microorganism further comprises a recombinantly expressd ornithine decarboxylase (ODC).

14. The modified microorganism of claim 12, wherein a gene encoding at least one polypeptide selected from the group consisting of ornithine carbamoyltransferase (ArgF) and putrescine acetyltransferase is inactivated.

15. The modified microorganism of claim 12, wherein the microorganism is *Corynebacterium glutamicum*.

16. A modified microorganism of the genus *Corynebacterium* wherein the microorganism produces arginine and recombinantly expresses the polypeptide of claim 1, and wherein the arginine producing ability of the microorganism is enhanced compared to the *Corynebacterium* microorganism that does not express the polypeptide of claim 1.

17. The modified microorganism of claim 16, wherein the microorganism (i) recombinantly expresses or (ii) shows an enhanced activity compared with the endogenous activity of at least one polypeptide selected from the group consisting of acetyl gamma-glutamyl-phosphate reductase (ArgC), acetylglutamate synthase or ornithine acetyltransferase (argJ), acetylglutamate kinase (ArgB), and acetylornithine aminotransferase (ArgD), wherein the (ii) enhancement of the activity is 1) increasing copy number of the polynucleotide encoding the polypeptide, 2) modifying expression regulatory sequence such that the expression of the polynucleotide is increased, 3) modifying the polynucleotide sequence on a chromosome such that the activity of the polypeptide is enhanced, 4) introducing a foreign polynucleotide exhibiting the activity of the polypeptide or a modified polynucleotide in which the codons of the above polynucleotide have been optimized, or 5) a combination thereof.

18. The modified microorganism of claim 16, wherein the microorganism (i) recombinantly expresses or (ii) shows an increased activity compared with the endogenous activity of at least one polypeptide selected from the group consisting of ornithine carbamoyltransfrase (ArgF), argininosuccinate synthase (argG), argininosuccinate lyase (argH), aspartate anmionia lyase (AAL) and aspartate aminotransferase (AST), wherein the (ii) enhancement of the activity is 1) increasing copy number of the polynucleotide encoding the polypeptide, 2) modifying expression regulatory sequence such that the expression of the polynucleotide is increased, 3) modifying the polynucleotide sequence on a chromosome such that the activity of the polypeptide is enhanced, 4) introducing a foreign polynucleotide exhibiting the activity of the polypeptide or a modified polynucleotide in which the codons of the above polynucleotide have been optimized, or 5) a combination thereof.

19. The modified microorganism of claim 16, wherein the microorganism is *Corynebacterium glutamicum*.

\* \* \* \* \*

SEQUENCE LISTING

<160> NUMBER OF SEQ ID NOS: 22

<210> SEQ ID NO 1
<211> LENGTH: 494
<212> TYPE: PRT
<213> ORGANISM: Artificial Sequence
<220> FEATURE:
<223> OTHER INFORMATION: ATCC13032 NCgl2522

<400> SEQUENCE: 1

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

-continued

Leu Cys Ile Trp Gly Ala Thr His Thr Asp Gly Leu Pro Phe Phe Ile
            355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 2
<211> LENGTH: 494
<212> TYPE: PRT
<213> ORGANISM: Artificial Sequence
<220> FEATURE:
<223> OTHER INFORMATION: ATCC13869 NCgl2522

<400> SEQUENCE: 2

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

-continued

```
Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
            245                 250                 255

Lys Ile Glu Glu Pro Leu Leu Asp Leu Ser Leu Phe Arg Asn Arg Leu
        260                 265                 270

Phe Leu Gly Gly Val Val Ala Ala Gly Met Ala Met Phe Thr Val Ser
    275                 280                 285

Gly Leu Glu Met Thr Thr Ser Gln Arg Phe Gln Leu Ser Val Gly Phe
290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
            325                 330                 335

Lys Pro Leu Ile Ser Gly Gly Phe Leu Ala Thr Ala Val Gly Ile Ala
        340                 345                 350

Leu Cys Ile Trp Gly Ala Thr His Thr Asp Gly Leu Pro Phe Phe Ile
    355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
            405                 410                 415

Val Ala Ile Leu Gly Ser Leu Phe Pro Phe Tyr Ser Leu His Ala
        420                 425                 430

Pro Ala Glu Val Ala Asp Asn Phe Ser Ala Gly Val His His Ala Ile
    435                 440                 445

Tyr Gly Asp Ala Ala Arg Ala Ser Leu Asp Thr Ala Tyr Ile Asn Val
450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
            485                 490
```

<210> SEQ ID NO 3
<211> LENGTH: 494
<212> TYPE: PRT
<213> ORGANISM: Artificial Sequence
<220> FEATURE:
<223> OTHER INFORMATION: NCgl2522_G77A (ATCC13032)

<400> SEQUENCE: 3

```
Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Ala Asp Lys Ile
65                  70                  75                  80

Gly His Arg Arg Met Phe Leu Met Gly Leu Ser Ile Phe Gly Ile Ala
            85                  90                  95
```

```
Ser Leu Gly Ala Ala Phe Ala Pro Thr Ala Trp Ala Leu Val Ala Ala
                100                 105                 110
Arg Ala Phe Leu Gly Ile Gly Ala Ala Thr Met Met Pro Ala Thr Leu
            115                 120                 125
Ala Leu Ile Arg Ile Thr Phe Glu Asp Glu Arg Glu Arg Asn Thr Ala
        130                 135                 140
Ile Gly Ile Trp Gly Ser Val Ala Ile Leu Gly Ala Ala Ala Gly Pro
145                 150                 155                 160
Ile Ile Gly Gly Ala Leu Leu Glu Phe Phe Trp Trp Gly Ser Val Phe
                165                 170                 175
Leu Ile Asn Val Pro Val Ala Val Ile Ala Leu Ile Ala Thr Leu Phe
            180                 185                 190
Val Ala Pro Ala Asn Ile Ala Asn Pro Ser Lys His Trp Asp Phe Leu
        195                 200                 205
Ser Ser Phe Tyr Ala Leu Leu Thr Leu Ala Gly Leu Ile Ile Thr Ile
210                 215                 220
Lys Glu Ser Val Asn Thr Ala Arg His Met Pro Leu Leu Gly Ala
225                 230                 235                 240
Val Ile Met Leu Ile Ile Gly Ala Val Leu Phe Ser Ser Arg Gln Lys
                245                 250                 255
Lys Ile Glu Glu Pro Leu Leu Asp Leu Ser Leu Phe Arg Asn Arg Leu
            260                 265                 270
Phe Leu Gly Gly Val Val Ala Ala Gly Met Ala Met Phe Thr Val Ser
        275                 280                 285
Gly Leu Glu Met Thr Thr Ser Gln Arg Phe Gln Leu Ser Val Gly Phe
290                 295                 300
Thr Pro Leu Glu Ala Gly Leu Leu Met Ile Pro Ala Ala Leu Gly Ser
305                 310                 315                 320
Phe Pro Met Ser Ile Ile Gly Gly Ala Asn Leu His Arg Trp Gly Phe
                325                 330                 335
Lys Pro Leu Ile Ser Gly Gly Phe Ala Ala Thr Ala Val Gly Ile Ala
            340                 345                 350
Leu Cys Ile Trp Gly Ala Thr His Thr Asp Gly Leu Pro Phe Phe Ile
        355                 360                 365
Ala Gly Leu Phe Phe Met Gly Ala Gly Ala Gly Ser Val Met Ser Val
            370                 375                 380
Ser Ser Thr Ala Ile Ile Gly Ser Ala Pro Val Arg Lys Ala Gly Met
385                 390                 395                 400
Ala Ser Ser Ile Glu Glu Val Ser Tyr Glu Phe Gly Thr Leu Leu Ser
                405                 410                 415
Val Ala Ile Leu Gly Ser Leu Phe Pro Phe Phe Tyr Ser Leu His Ala
            420                 425                 430
Pro Ala Glu Val Ala Asp Asn Phe Ser Ala Gly Val His His Ala Ile
        435                 440                 445
Asp Gly Asp Ala Ala Arg Ala Ser Leu Asp Thr Ala Tyr Ile Asn Val
    450                 455                 460
Leu Ile Ile Ala Leu Val Cys Ala Val Ala Ala Leu Ile Ser Ser
465                 470                 475                 480
Tyr Leu Phe Arg Gly Asn Pro Lys Gly Ala Asn Asn Ala His
                485                 490
```

-continued

```
<210> SEQ ID NO 4
<211> LENGTH: 494
<212> TYPE: PRT
<213> ORGANISM: Artificial Sequence
<220> FEATURE:
<223> OTHER INFORMATION: NCgl2522_G77R (ATCC13032)

<400> SEQUENCE: 4

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Gly Thr Gly Thr Leu Arg Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365
```

```
Ala Gly Leu Phe Phe Met Gly Ala Gly Ala Gly Ser Val Met Ser Val
    370                 375                 380
Ser Ser Thr Ala Ile Ile Gly Ser Ala Pro Val Arg Lys Ala Gly Met
385                 390                 395                 400
Ala Ser Ser Ile Glu Glu Val Ser Tyr Glu Phe Gly Thr Leu Leu Ser
                405                 410                 415
Val Ala Ile Leu Gly Ser Leu Phe Pro Phe Phe Tyr Ser Leu His Ala
                420                 425                 430
Pro Ala Glu Val Ala Asp Asn Phe Ser Ala Gly Val His His Ala Ile
                435                 440                 445
Asp Gly Asp Ala Ala Arg Ala Ser Leu Asp Thr Ala Tyr Ile Asn Val
450                 455                 460
Leu Ile Ile Ala Leu Val Cys Ala Val Ala Ala Leu Ile Ser Ser
465                 470                 475                 480
Tyr Leu Phe Arg Gly Asn Pro Lys Gly Ala Asn Asn Ala His
                485                 490

<210> SEQ ID NO 5
<211> LENGTH: 494
<212> TYPE: PRT
<213> ORGANISM: Artificial Sequence
<220> FEATURE:
<223> OTHER INFORMATION: NCgl2522_G77A (ATCC13869)

<400> SEQUENCE: 5

Met Ile Ser Glu Thr Leu Gln Ala Gln Ala Pro Thr Lys Thr Gln Arg
1               5                   10                  15
Trp Ala Phe Leu Ala Val Ile Ser Gly Gly Leu Phe Leu Ile Gly Val
                20                  25                  30
Asp Asn Ser Ile Leu Tyr Thr Ala Leu Pro Leu Leu Arg Glu Gln Leu
                35                  40                  45
Ala Ala Thr Glu Thr Gln Ala Leu Trp Ile Ile Asn Ala Tyr Pro Leu
    50                  55                  60
Leu Met Ala Gly Leu Leu Leu Gly Thr Gly Thr Leu Ala Asp Lys Ile
65                  70                  75                  80
Gly His Arg Arg Met Phe Leu Met Gly Leu Ser Ile Phe Gly Ile Ala
                85                  90                  95
Ser Leu Gly Ala Ala Phe Ala Pro Thr Ala Trp Ala Leu Val Ala Ala
                100                 105                 110
Arg Ala Phe Leu Gly Ile Gly Ala Ala Thr Met Met Pro Ala Thr Leu
                115                 120                 125
Ala Leu Ile Arg Ile Thr Phe Glu Asp Glu Arg Glu Arg Asn Thr Ala
    130                 135                 140
Ile Gly Ile Trp Gly Ser Val Ala Ile Leu Gly Ala Ala Ala Gly Pro
145                 150                 155                 160
Ile Ile Gly Gly Ala Leu Leu Glu Phe Phe Trp Trp Gly Ser Val Phe
                165                 170                 175
Leu Ile Asn Val Pro Val Ala Val Ile Ala Leu Ile Ala Thr Leu Phe
                180                 185                 190
Val Ala Pro Ala Asn Ile Ala Asn Pro Ser Lys His Trp Asp Phe Leu
                195                 200                 205
Ser Ser Phe Tyr Ala Leu Leu Thr Leu Ala Gly Leu Ile Val Thr Ile
    210                 215                 220
Lys Glu Ser Val Asn Thr Ala Arg His Leu Pro Leu Leu Val Gly Ala
225                 230                 235                 240
```

```
Ile Ile Leu Leu Ile Ile Gly Ala Val Leu Phe Ser Ser Arg Gln Lys
            245                 250                 255

Lys Ile Glu Glu Pro Leu Leu Asp Leu Ser Leu Phe Arg Asn Arg Leu
        260                 265                 270

Phe Leu Gly Gly Val Val Ala Ala Gly Met Ala Met Phe Thr Val Ser
    275                 280                 285

Gly Leu Glu Met Thr Thr Ser Gln Arg Phe Gln Leu Ser Val Gly Phe
290                 295                 300

Thr Pro Leu Glu Ala Gly Leu Leu Met Ile Pro Ala Ala Leu Gly Ser
305                 310                 315                 320

Phe Pro Met Ser Ile Ile Gly Ala Asn Leu His Arg Trp Gly Phe
            325                 330                 335

Lys Pro Leu Ile Ser Gly Gly Phe Leu Ala Thr Ala Val Gly Ile Ala
        340                 345                 350

Leu Cys Ile Trp Gly Ala Thr His Thr Asp Gly Leu Pro Phe Ile
    355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
            405                 410                 415

Val Ala Ile Leu Gly Ser Leu Phe Pro Phe Phe Tyr Ser Leu His Ala
        420                 425                 430

Pro Ala Glu Val Ala Asp Asn Phe Ser Ala Gly Val His His Ala Ile
    435                 440                 445

Tyr Gly Asp Ala Ala Arg Ala Ser Leu Asp Thr Ala Tyr Ile Asn Val
450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Ala His
            485                 490
```

<210> SEQ ID NO 6
<211> LENGTH: 494
<212> TYPE: PRT
<213> ORGANISM: Artificial Sequence
<220> FEATURE:
<223> OTHER INFORMATION: NCgl2522_G77R (ATCC13869)

<400> SEQUENCE: 6

```
Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Thr Gly Thr Leu Arg Asp Lys Ile
65                  70                  75                  80

Gly His Arg Arg Met Phe Leu Met Gly Leu Ser Ile Phe Gly Ile Ala
            85                  90                  95

Ser Leu Gly Ala Ala Phe Ala Pro Thr Ala Trp Ala Leu Val Ala Ala
        100                 105                 110
```

-continued

Arg Ala Phe Leu Gly Ile Gly Ala Ala Thr Met Met Pro Ala Thr Leu
115                 120                 125

Ala Leu Ile Arg Ile Thr Phe Glu Asp Glu Arg Glu Arg Asn Thr Ala
130                 135                 140

Ile Gly Ile Trp Gly Ser Val Ala Ile Leu Gly Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
                180                 185                 190

Val Ala Pro Ala Asn Ile Ala Asn Pro Ser Lys His Trp Asp Phe Leu
                195                 200                 205

Ser Ser Phe Tyr Ala Leu Leu Thr Leu Ala Gly Leu Ile Val Thr Ile
210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
                260                 265                 270

Phe Leu Gly Gly Val Val Ala Ala Gly Met Ala Met Phe Thr Val Ser
                275                 280                 285

Gly Leu Glu Met Thr Thr Ser Gln Arg Phe Gln Leu Ser Val Gly Phe
                290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
                340                 345                 350

Leu Cys Ile Trp Gly Ala Thr His Thr Asp Gly Leu Pro Phe Phe Ile
                355                 360                 365

Ala Gly Leu Phe Phe Met Gly Ala Gly Ala Gly Ser Val Met Ser Val
370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
                420                 425                 430

Pro Ala Glu Val Ala Asp Asn Phe Ser Ala Gly Val His His Ala Ile
                435                 440                 445

Tyr Gly Asp Ala Ala Arg Ala Ser Leu Asp Thr Ala Tyr Ile Asn Val
                450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 7
<211> LENGTH: 36
<212> TYPE: DNA
<213> ORGANISM: Artificial Sequence
<220> FEATURE:
<223> OTHER INFORMATION: Primer 13032-putE-EF-FX

<400> SEQUENCE: 7
ccggggatcc tctagaactt cagaaacctt acaggc                          36

<210> SEQ ID NO 8
<211> LENGTH: 36
<212> TYPE: DNA
<213> ORGANISM: Artificial Sequence
<220> FEATURE:
<223> OTHER INFORMATION: Primer 13032-putE-EF-RX

<400> SEQUENCE: 8
gcaggtcgac tctagactag tgcgcattat tggctc                          36

<210> SEQ ID NO 9
<211> LENGTH: 24
<212> TYPE: DNA
<213> ORGANISM: Artificial Sequence
<220> FEATURE:
<223> OTHER INFORMATION: Primer SM_putE_G77-F
<220> FEATURE:
<221> NAME/KEY: misc_feature
<222> LOCATION: (1)...(24)
<223> OTHER INFORMATION: n = A,T,C or G

<400> SEQUENCE: 9
ccggcacttt gnnkgacaaa atcg                                       24

<210> SEQ ID NO 10
<211> LENGTH: 24
<212> TYPE: DNA
<213> ORGANISM: Artificial Sequence
<220> FEATURE:
<223> OTHER INFORMATION: Primer SM_putE_G77-R
<220> FEATURE:
<221> NAME/KEY: misc_feature
<222> LOCATION: (1)...(24)
<223> OTHER INFORMATION: n = A,T,C or G

<400> SEQUENCE: 10 cgatttgtc mnncaaagtg ccgg                                        24

<210> SEQ ID NO 11
<211> LENGTH: 34
<212> TYPE: DNA
<213> ORGANISM: Artificial Sequence
<220> FEATURE:
<223> OTHER INFORMATION: Primer pDC-Pself-putE-up-FX

<400> SEQUENCE: 11
ccggggatcc tctagacctc taagcgcctc aaag                            34

<210> SEQ ID NO 12
<211> LENGTH: 34
<212> TYPE: DNA
<213> ORGANISM: Artificial Sequence
<220> FEATURE:
<223> OTHER INFORMATION: Primer pDC-putE-up-RX

<400> SEQUENCE: 12
gcaggtcgac tctagagatt cgcgatattg gccg                            34

<210> SEQ ID NO 13
<211> LENGTH: 24
<212> TYPE: DNA
<213> ORGANISM: Artificial Sequence
<220> FEATURE:
<223> OTHER INFORMATION: Primer putE-G77A-F

<400> SEQUENCE: 13
ccggcacttt ggctgacaaa atcg                                          24

<210> SEQ ID NO 14
<211> LENGTH: 24
<212> TYPE: DNA
<213> ORGANISM: Artificial Sequence
<220> FEATURE:
<223> OTHER INFORMATION: Primer putE-G77A-R

<400> SEQUENCE: 14
cgattttgtc agccaaagtg ccgg                                          24

<210> SEQ ID NO 15
<211> LENGTH: 24
<212> TYPE: DNA
<213> ORGANISM: Artificial Sequence
<220> FEATURE:
<223> OTHER INFORMATION: Primer putE-G77R-F

<400> SEQUENCE: 15
ccggcacttt gcgtgacaaa atcg                                          24

<210> SEQ ID NO 16
<211> LENGTH: 24
<212> TYPE: DNA
<213> ORGANISM: Artificial Sequence
<220> FEATURE:
<223> OTHER INFORMATION: Primer putE-G77R-R

<400> SEQUENCE: 16
cgattttgtc acgcaaagtg ccgg                                          24

<210> SEQ ID NO 17
<211> LENGTH: 37
<212> TYPE: DNA
<213> ORGANISM: Artificial Sequence
<220> FEATURE:
<223> OTHER INFORMATION: Primer NCgl2522-L5

<400> SEQUENCE: 17
tgcaggtcga ctctagagtt ctgcgtagct gtgtgcc                            37

<210> SEQ ID NO 18
<211> LENGTH: 31
<212> TYPE: DNA
<213> ORGANISM: Artificial Sequence
<220> FEATURE:
<223> OTHER INFORMATION: Primer NCgl2522-L3

<400> SEQUENCE: 18
gatgtttctg gatcgtaact gtaacgaatg g                                  31

<210> SEQ ID NO 19
<211> LENGTH: 24
<212> TYPE: DNA
<213> ORGANISM: Artificial Sequence
<220> FEATURE:
<223> OTHER INFORMATION: Primer CJ7-F

<400> SEQUENCE: 19
agaaacatcc cagcgctact aata                                          24

```
<210> SEQ ID NO 20
<211> LENGTH: 23
<212> TYPE: DNA
<213> ORGANISM: Artificial Sequence
<220> FEATURE:
<223> OTHER INFORMATION: Primer CJ7-R

<400> SEQUENCE: 20
agtgtttcct ttcgttgggt acg                                             23

<210> SEQ ID NO 21
<211> LENGTH: 41
<212> TYPE: DNA
<213> ORGANISM: Artificial Sequence
<220> FEATURE:
<223> OTHER INFORMATION: Primer NCgl2522-R5

<400> SEQUENCE: 21
caacgaaagg aaacactatg atttcagaaa ctttgcaggc g                         41

<210> SEQ ID NO 22
<211> LENGTH: 40
<212> TYPE: DNA
<213> ORGANISM: Artificial Sequence
<220> FEATURE:
<223> OTHER INFORMATION: Primer NCgl2522-R3

<400> SEQUENCE: 22
tcggtacccg gggatcccac aaaaagcgta gcgatcaacg                           40
```